US012599854B2

(12) United States Patent
Yamamoto et al.

(10) Patent No.: US 12,599,854 B2
(45) Date of Patent: Apr. 14, 2026

(54) FILTRATION DEVICE, FILTRATION METHOD AND FILTRATION FILTER

(71) Applicant: Murata Manufacturing Co., Ltd., Nagaokakyo (JP)

(72) Inventors: Wataru Yamamoto, Nagaokakyo (JP); Takashi Kondo, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 492 days.

(21) Appl. No.: 15/484,521

(22) Filed: Apr. 11, 2017

(65) Prior Publication Data

US 2017/0216743 A1      Aug. 3, 2017

Related U.S. Application Data

(63) Continuation of application No. PCT/JP2016/067691, filed on Jun. 14, 2016.

(30) Foreign Application Priority Data

Jun. 22, 2015    (JP) ................................. 2015-124780

(51) Int. Cl.
B01D 29/00          (2006.01)
B01D 29/96          (2006.01)
(Continued)

(52) U.S. Cl.
CPC ......... B01D 29/96 (2013.01); B01D 29/0097 (2013.01); B01D 33/04 (2013.01);
(Continued)

(58) Field of Classification Search
CPC .... B01D 29/96; B01D 29/0097; B01D 33/04; B01D 46/00; B01D 46/103; B01D 46/16;
(Continued)

(56) References Cited

U.S. PATENT DOCUMENTS 2,563,422 A * 8/1951 Sabo ....................... A47J 45/10
                                                          294/99.2
2,675,129 A * 4/1954 Doubleday .......... B01D 33/048
                                                          210/106
(Continued)

FOREIGN PATENT DOCUMENTS

JP          S63-18680 U      2/1978
JP          S62-75817 U      5/1987
(Continued)

OTHER PUBLICATIONS

International Search Report issued in International Application No. PCT/JP2016/067691, date of mailing Sep. 13, 2016.
(Continued)

*Primary Examiner* — T. Bennett McKenzie
(74) *Attorney, Agent, or Firm* — ArentFox Schiff LLP

(57) ABSTRACT

Provided is a filtration device that can increase a filtration treatment amount by suppressing clogging of a filtration filter. A filtration device according to the present invention includes: a filtration filter that includes a filter that filters a filtration target contained in a fluid, and a frame that holds the filter; a support structure that holds the frame such that the filter is bent; and a fluid supplying unit that supplies the fluid with the filter being in a bent state.

25 Claims, 10 Drawing Sheets

2

(51) Int. Cl.

| | |
|---|---|
| *B01D 33/04* | (2006.01) |
| *B01D 46/10* | (2006.01) |
| *B01D 46/16* | (2006.01) |
| *B01D 46/22* | (2006.01) |
| *B01D 63/14* | (2006.01) |
| *B01D 65/08* | (2006.01) |
| *C12M 1/00* | (2006.01) |

(52) U.S. Cl.

CPC .......... *B01D 46/103* (2013.01); *B01D 46/16* (2013.01); *B01D 46/22* (2013.01); *B01D 63/14* (2013.01); *B01D 65/08* (2013.01); *C12M 29/04* (2013.01); *B01D 2201/04* (2013.01); *B01D 2313/025* (2013.01)

(58) Field of Classification Search

CPC ........ B01D 46/22; B01D 63/14; B01D 63/08; B01D 69/087; B01D 2201/04; B01D 2313/025; B01D 33/0022–0029; B01D 33/0041; B01D 33/0058; B01D 33/015–0166; B01D 33/048; B01D 24/28–32; B01D 24/34; B01D 25/127–1275; B01D 65/08; B01D 2313/2031; C12M 29/04; C12M 37/02; C12M 47/00–18; C12M 1/123; C12M 1/128; C12M 3/062; C12M 3/067; C12M 25/02–04; C12M 33/14

USPC .......... 95/273–287; 210/160, 400, 526, 783, 210/273–287, 464–469; 55/351–354, 55/490–519

See application file for complete search history.

(56) References Cited

U.S. PATENT DOCUMENTS

| | | | | |
|---|---|---|---|---|
| 3,221,479 A | * | 12/1965 | Moser .................... | B01D 46/18 55/296 |
| 3,648,381 A | * | 3/1972 | Fox ......................... | D06F 58/22 34/82 |
| 3,678,240 A | * | 7/1972 | Dietrick ................... | B23H 1/10 219/69.14 |
| 3,897,341 A | * | 7/1975 | Ozawa ................. | B01D 33/048 210/386 |
| 3,931,012 A | * | 1/1976 | Huse ...................... | B01D 33/04 210/251 |
| 3,951,805 A | * | 4/1976 | Dodd .................... | B01D 37/02 210/193 |
| 4,443,897 A | * | 4/1984 | Austin ..................... | E03C 1/26 4/291 |
| 4,501,040 A | * | 2/1985 | Biondetti .............. | B01D 35/28 162/318 |
| 4,861,495 A | * | 8/1989 | Pietzsch ............... | B01D 33/042 210/739 |
| 5,891,207 A | * | 4/1999 | Katta ................. | B01D 46/0002 55/385.3 |
| 5,914,038 A | * | 6/1999 | Orizand .............. | B01D 36/001 210/401 |
| 6,143,133 A | * | 11/2000 | Gommel ................ | B01D 33/64 162/208 |
| 6,171,853 B1 | * | 1/2001 | Kim ....................... | B01D 53/85 435/299.1 |

| | | | | |
|---|---|---|---|---|
| 6,221,120 B1 | * | 4/2001 | Bennington ........... | B01D 46/10 55/385.1 |
| 6,547,080 B1 | * | 4/2003 | Guard ..................... | A47J 47/20 210/473 |
| 6,555,013 B2 | * | 4/2003 | Nakamura ............ | B01D 33/04 210/769 |
| 7,174,830 B1 | * | 2/2007 | Dong ..................... | B25J 9/0087 99/348 |
| 7,951,292 B1 | * | 5/2011 | De La Torre .......... | E03C 1/264 210/164 |
| 9,688,465 B2 | * | 6/2017 | Trombetta .............. | B65B 55/24 |
| 9,963,679 B2 | | 5/2018 | Taylor et al. | |
| 2001/0054592 A1 | * | 12/2001 | Day ..................... | B01D 33/466 210/783 |
| 2003/0235920 A1 | | 12/2003 | Wyatt et al. | |
| 2004/0000160 A1 | * | 1/2004 | Takashima ........... | B01D 46/681 62/262 |
| 2005/0023040 A1 | * | 2/2005 | Cabelka .................. | E21B 21/01 210/519 |
| 2006/0060522 A1 | * | 3/2006 | Bushey ................... | A47J 43/24 210/470 |
| 2006/0096929 A1 | * | 5/2006 | Repp ...................... | A47J 19/00 210/740 |
| 2007/0180610 A1 | * | 8/2007 | Mohr ...................... | E03C 1/186 4/655 |
| 2008/0053890 A1 | * | 3/2008 | McDonald ........... | A47J 19/005 210/469 |
| 2008/0086812 A1 | * | 4/2008 | Yu ............................. | E03C 1/18 4/639 |
| 2011/0274801 A1 | * | 11/2011 | Haber ..................... | B32B 25/20 426/431 |
| 2012/0055515 A1 | * | 3/2012 | de Raddo .............. | A47J 43/24 134/25.3 |
| 2012/0107936 A1 | | 5/2012 | Taylor et al. | |
| 2013/0260625 A1 | * | 10/2013 | Ramirez ................. | D06F 58/22 442/110 |
| 2013/0283521 A1 | * | 10/2013 | Jain ......................... | E03C 1/186 4/654 |
| 2015/0217458 A1 | * | 8/2015 | Nammoto .............. | B25J 13/087 414/737 |
| 2016/0195458 A1 | | 7/2016 | Kikuhara et al. | |

FOREIGN PATENT DOCUMENTS

| | | |
|---|---|---|
| JP | S63-77502 A | 4/1988 |
| JP | H01-174010 U | 12/1989 |
| JP | H04-61903 A | 2/1992 |
| JP | H09-230056 A | 9/1997 |
| JP | 3050522 B | 7/1998 |
| JP | 2001-27586 A | 1/2001 |
| JP | 2003-103118 A | 4/2003 |
| JP | 2006-95499 A | 4/2006 |
| JP | 2006518462 A | 8/2006 |
| JP | 2007-152223 A | 6/2007 |
| JP | 2012065590 A | 4/2012 |
| JP | 2013543725 A | 12/2013 |
| WO | WO 2015-019889 A1 | 2/2015 |

OTHER PUBLICATIONS

Written Opinion of the International Searching Authority issued in International Application No. PCT/JP2016/067691, date of mailing Sep. 13, 2016.

* cited by examiner

FILTRATION DEVICE, FILTRATION METHOD AND FILTRATION FILTER

CROSS REFERENCE TO RELATED APPLICATIONS

The present application is a continuation of International application No. PCT/JP2016/067691, filed on Jun. 14, 2016, which claims priority to Japanese Patent Application No. 2015-124780, filed on Jun. 22, 2015, the entire contents of each of which are incorporated herein by reference.

TECHNICAL FIELD

The present invention relates to a filtration device, a filtration method and a filtration filter that filter a filtration target contained in a fluid.

BACKGROUND OF THE INVENTION

A known filtration filter that filters a biological product contained in a liquid is disclosed in International Publication No. 2015/019889. This publication discloses a filtration filter The filtration filter is installed such that a tensile force acts from the center thereof toward an outer peripheral portion thereof and such that the outer peripheral portion thereof is fitted between a cover member and a receiving member. In this state, a liquid containing a biological product is made to pass through the filtration filter, and as a result, the biological product is filtered.

SUMMARY OF INVENTION

As filtration of filtration target such as a biological product proceeds, clogging of the filtration filter occurs. When the filtration filter is clogged, it is no longer possible to continue filtering the filtration target.

BRIEF SUMMARY OF THE INVENTION

In order to solve the above-described problem, an object of the present invention is to provide a filtration device, a filtration method and a filtration filter that can increase a filtration treatment amount by suppressing clogging of a filtration filter.

The presently preferred embodiments include the following.

A filtration device comprising a filter assembly including a frame which holds a filter, a support structure that holds the frame such that the filter is bent and a fluid supply that supplies a fluid containing a filtration target to the filter while the filter is in a bent state whereby the filter filters a filtration target contained in the fluid.

The filter is preferably planar before the frame is held by the support structure and is bent into a non-planar shape by the support structure. The bending amount of the filter caused by the frame being held by the support structure is preferably larger than a bending amount of the filter caused by pressure of the fluid passing through the filter. The support structure preferably holds the frame in such a manner that the filter is bent toward a side that receives the pressure of the fluid. The support structure preferably allows the amount that the filter is bent to be adjusted.

The filtration target is, for example, a biological product and the filter is, for example, a metal thin film having a plurality of through holes that separate the biological product from the fluid.

In another preferred embodiment of the invention, a filtration device includes a frame that supports a plurality of filters at spaced locations, a fluid supply that supplies a fluid containing a filtration target to be filtered to a filtering area and a conveyer that supports the frame and moves a set of the filters into the filtering area. The conveyor moves the set of filter in such a manner that the fluid passes through the set of filters located in the filtering area. The conveyer bends the frame, and with it the set of filters located in the filtering area, such that the fluid is passed through the set of bent filters located in the filtering area while they are in the bent state.

The set of filters can include one or more filters. The conveyer preferably sequentially moves different sets of filters into the filtering area. The filters are preferably planar before they are moved into the filtering area and are bent into a non-planar shape by the conveyer when they are located in the filtering area.

The bending amount of the filters located in the filtering area caused by the frame being bent by the conveyer is preferably larger than a bending amount of the filters located in the filtering area caused by pressure of the fluid passing through the filters located in the filtering area. The conveyer preferably allows the amount that the frame, and therefore the amount of the filters, located in the filtering area is bent to be adjusted.

The filtration target is preferably a biological product and the filters are preferably metal thin films having a plurality of through holes that separate the biological product from the fluid. The frame is preferably a flexible tape-shaped member and the filters are provided at spaced locations along a longitudinal direction of the tape-shaped member. The conveyer can cause the frame to deform in a wave-like manner when it is located in the filtering area.

According to the present invention, a filtration treatment amount can be increased by suppressing clogging of the filtration filter.

DESCRIPTION OF THE PREFERRED EMBODIMENTS (Findings that are Basis of Present Invention)

The present inventors obtained the following findings as a result of performing intensive studies in order to increase the filtration treatment amount compared with that of filtration devices of the related art.

Figure 21:
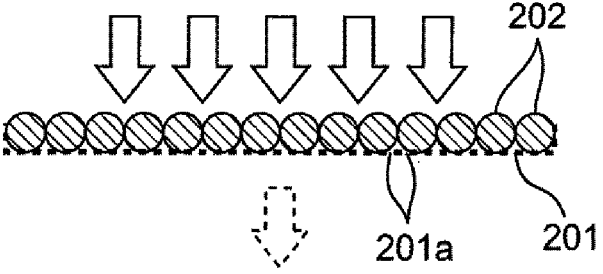
FIG. 21 is a schematic diagram illustrating a situation in which a liquid that contains a filtration target is supplied to a filtration filter assuming a flat posture.
Figure 22:
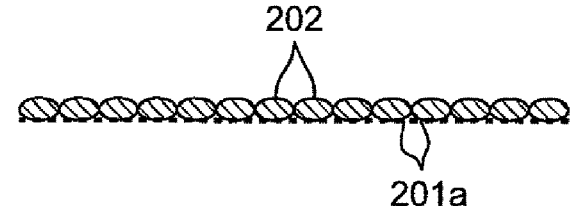
FIG. 22 is a schematic diagram illustrating a state in which a biological product, which is a filtration target, presses against a filtration filter assuming a flat posture and deformed into a flat shape.

As illustrated in FIG. 21, a filtration filter 201 becomes clogged when all (or substantially all) of a plurality of through holes 201a provided in the filtration filter 201 becomes blocked by a filtration target 202. In particular, in the case where the filtration target 202 is a biological product, since particles of biological products have high deformability, particles of the filtration target 202 readily deform into a flat shape when undergoing filtration as illustrated in FIG. 22. In other words, particles of the biological product initially have a substantially spherical shape within a liquid, but the biological product is suddenly decelerated by a main surface of the filtration filter 201, which is perpendicular to a flow direction of the fluid when filtration is performed, and presses against the main surface. As a result, the particles of the biological product readily deform into a flat shape. In this case, one particle of the filtration target 202, which has deformed into a flat shape, blocks a plurality of through holes 201a and clogging is even more likely to occur.

Figure 23:
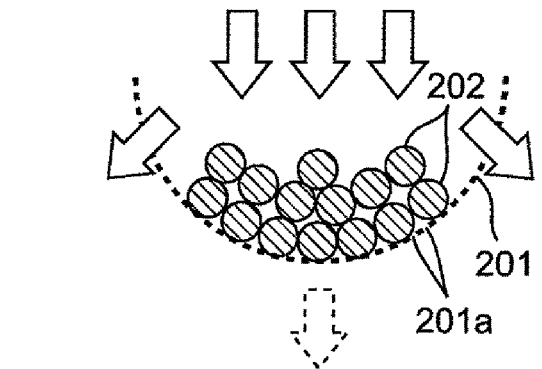
FIG. 23 is a schematic diagram illustrating a situation in which a liquid containing a biological product is supplied in a state where a filtration filter is bent toward a side that does not receive the pressure of the liquid.
Figure 24:
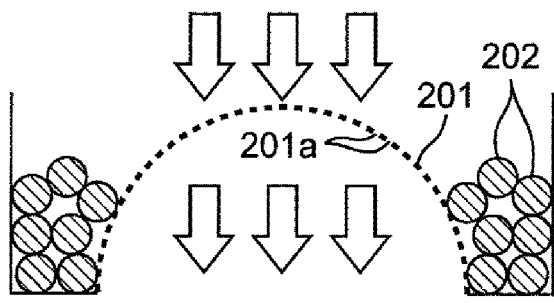
FIG. 24 is a schematic diagram illustrating a situation in which a liquid containing a biological product is supplied in a state where a filtration filter is bent toward a side that receives the pressure of the liquid.

In the filtration device of the related art, since the filtration filter 201 is installed such that a tensile force acts from the center thereof toward an outer peripheral portion thereof, the filtration filter 201 does not bend and assumes a flat posture. In contrast, and as illustrated in FIG. 23, the present inventors found that the through holes 201a in an outer peripheral portion of the filtration filter 201 are not blocked when the filtration filter 201 is made to filter the same amount of the filtration target 202 in a state where the filtration filter 201 is bent toward a side that does not receive the pressure of the liquid. The present inventors additionally found that since the speed of the flowing filtration target 202 is gently reduced by the curved surface of the filtration filter 201, particles of the filtration target 202 are captured by the filtration filter 201 in a state of being in a flat shape that is close to the substantially spherical shape of the particles within the liquid (i.e., before filtering). In this case, blocking of a plurality of through holes 201a by one particle of the filtration target 202 can be suppressed. In addition, as illustrated in FIG. 24, the present inventors found that the through holes 201a in a central part of the filtration filter 201 are not blocked when the filtration filter 201 is made to filter the same amount of the filtration target 202 in a state where the filtration filter 201 is bent toward a side that receives the pressure of the liquid. In other words, the present inventors found that it is possible to increase the amount of the filtration target that would be required to block all the through holes 201a and to increase the filtration treatment amount by performing filtration in a state where the filtration filter 201 is actively (forcibly) bent. The present inventors arrived at the following invention on the basis of these novel findings.

Hereafter, preferred embodiments of the present invention will be described in detail with reference to the drawings.

Embodiment 1

Figure 1:
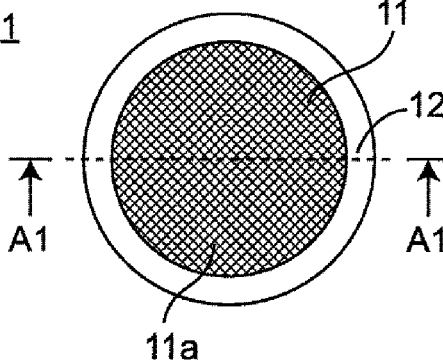
FIG. 1 is a schematic plan view of a filtration filter used in a filtration device according to embodiment 1 of the present invention.
Figure 2:
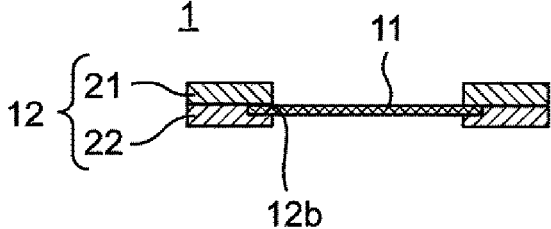
FIG. 2 is a sectional view taken along line A1-A1 in FIG. 1.

As shown in FIGS. 1 and 2, in embodiment 1 a filtration target is a biological product contained in a liquid. In this specification, the term "biological product" refers to a substance derived from a living thing such as a cell (eukaryote), a bacterium (eubacterium), a virus or the like. Examples of a cell (eukaryote) include an ovum, a spermatozoon, an induced pluripotent stem cell (iPS cell), an ES cell, a stem cell, a mesenchymal stem cell, a monocytic cell, a single cell, a cell aggregation, a floating cell, an adhesive cell, a nerve cell, a blood cell, a lymphocyte, a regenerative medicine cell, an autologous cell, a cancer cell, a circulating tumor cell (CTC), a HL-60, a HELA and fungi. Examples of bacteria (eubacteria) include gram positive bacteria, gram negative bacteria, $E.$ $coli$ and a tubercle $bacillus$. Examples of a virus include a DNA virus, an RNA virus, a rotavirus, an (avian) influenza virus, a yellow fever virus, a dengue fever virus, an encephalitis virus, a hemorrhagic fever virus and an immunodeficiency virus.

As illustrated in FIG. 1, a filtration filter 1 according to embodiment 1 includes a filter 11 and a frame 12 that holds the filter 11.

The filter 11 is preferably formed of a circular metal thin film. Examples of the material of the filter 11 include gold, silver, copper, platinum, nickel, stainless steel, palladium, titanium, cobalt, and alloys of these metals. It is preferable that the material of the filter 11 be a material that can be sterilized in a variety of ways such as through gamma ray irradiation, an autoclave and ethylene gas. In addition, the filter 11 may be a resin thin film, a paper filter, or the like. In other words, it is sufficient that the filter 11 be a porous membrane. The filter 11 has, for example, a diameter of 8 mm and a thickness of 1.2 μm. The thickness of the filter 11 is preferably 100 nm to 100 μm and more preferably 500 nm to 30 μm so that the filter 11 has an appropriate degree of flexibility.

The filter 11 has a pair of opposing main surfaces and has a plurality of through holes 11a that penetrate through both main surfaces. The shape and dimensions of the through holes 11a are appropriately set in accordance with the shape and size of the biological product to be filtered out of a liquid (more generally, a fluid). The through holes 11a can be regularly or periodically arranged. The through holes 11a can have a square shape when viewed from a main surface side of the filter 11. In such a case, the size of the through holes 11a is preferably 0.1-500 μm in a longitudinal direction and 0.1-500 μm in a lateral direction. The interval between the through holes 11a is preferably ten times an opening diameter of the through holes 11a or less, and more preferably, is preferably no more than three times the opening diameter. In addition, an opening ratio of the through holes 11a with respect to the filter 11 is for example 10% or higher.

In embodiment 1, the frame 12 is formed of a flexible material. Examples of the material of the frame 12 include polypropylene, polyester, polyurethane, rayon, polyvinyl chloride, hydrogel, nylon, polyolefin and paper. It is preferable that the material of the frame 12 be a material that can be sterilized in a variety of ways such as through gamma ray irradiation, an autoclave and ethylene gas. Examples of such a material include polyester, polyurethane and polyvinyl chloride. The width of the frame 12 is 3.9 mm, for example. The thickness of the frame 12 is 3.0 mm, for example.

In embodiment 1, the frame 12 has a two-layer structure, and is formed of a first layer member 21 and a second layer member 22. The first layer member 21 is connected to one main surface of the filter 11 with, for example, an adhesive. The second layer member 22 is connected to the other main surface of the filter 11 with, for example, an adhesive. In other words, the frame 12 is connected to both opposed main surfaces of the filter 11. Thus, the filter 11 can be prevented from peeling off the frame 12 when the filtration filter 1 is bent. The first layer member 21 and the second layer member 22 are connected to each other with, for example, an adhesive. The adhesive is preferably a non-water-soluble adhesive. Examples of such an adhesive include an epoxy based adhesive and a silylated-urethane-resin-based adhesive.

The frame 12 is formed in an annular shape. A recess 12b is provided in an inner peripheral wall of the frame 12. The recess 12b is formed in, for example, an annular shape. An outer peripheral portion of the filter 11 is fitted into the recess 12b and the filter 11 is thus held by the frame 12. By providing the recess 12b, shifting of the position of the filter 11 can be suppressed, for example. It is sufficient for the recess 12b to be provided in at least either of the first layer member 21 and the second layer member 22.

Figure 3:
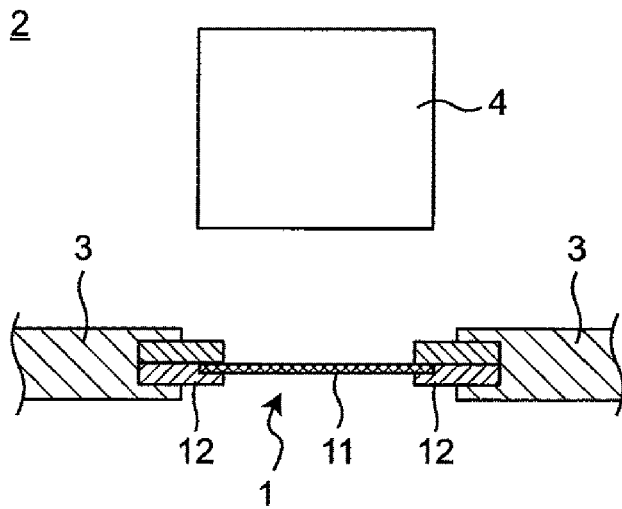
FIG. 3 is a schematic sectional view of the filtration device according to embodiment 1 of the present invention.
Figure 4:
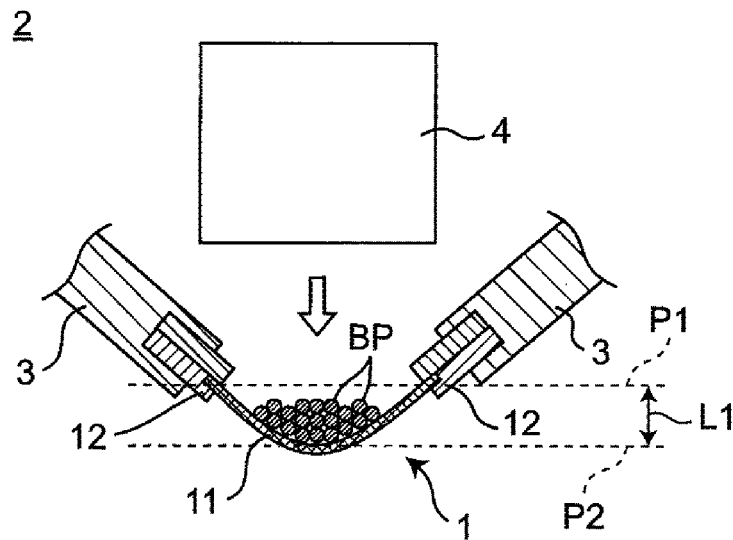
FIG. 4 is a sectional view illustrating a state in which support structures hold a frame in the filtration device illustrated in FIG. 3 such that a filter is bent toward a side that does not receive the pressure of a liquid.

Next, description will be given of a filtration device 2 that filters a biological product by using the filtration filter 1 according to embodiment 1. FIG. 3 is a sectional view illustrating a schematic configuration of the filtration device 2. FIG. 4 is a sectional view of the filtration device 2 illustrating a state in which the filter 11 is bent. Operation of the filtration device 2 is controlled by a control unit provided in the filtration device 2 on the basis of a program that is stored in advance.

As illustrated in FIG. 3, the filtration device 2 includes support structures 3 that hold the frame 12, and a fluid supplying unit 4 that supplies a liquid containing a biological product BP to the filter 11.

As illustrated in FIG. 4, the support structures 3 are configured to hold the frame 12 such that the filter 11 is bent with respect to a plane P1 that intersects (for example, is perpendicular to) the direction in which the fluid is supplied. The fluid supplying unit 4 supplies the liquid containing the biological product BP to the filter 11 with the filter 11 being in a bent state. Thus, the filter 11 filters the biological product BP contained in the liquid.

According to embodiment 1, the fluid supplying unit supplies the liquid containing the biological product BP in a state where the support structures 3 bend the filter 11, and therefore the amount of biological product BP that would be required to block all the through holes 11a of the filter 11 can be increased. Thus, blocking of the through holes 11a in a peripheral portion of the filter 11 by the biological product BP is suppressed, and consequently, clogging of the filtration filter 1 can be suppressed. As a result, the filtration treatment amount of the filtration filter 1 can be increased compared with the related art. Here, "bending" does not only refer to bending in an arc-like shape. For example, the meaning of "bending" also includes bending (curving) at an acute angle, a right angle and an obtuse angle.

It is preferable that the bending amount of the filter 11 that is caused by the frame 12 being held by the support structures 3 be larger than the bending amount of the filter 11 caused by the pressure of the liquid. For example, as illustrated in FIG. 4, the support structures 3 preferably hold the frame 12 such that a bending amount L1 of an exposed portion of the filter 11 that is not held by the frame 12 is at least two times the average particle diameter of the biological product BP. With this configuration, the filtration treatment amount can be further increased by suppressing clogging of the filtration filter 1 even more. "Bending amount" refers to the distance from the plane P1 that extends through outer peripheral end portions of the exposed portion of the filter 11 (portions where the frame 12 and filter 11 are connected to each other) to a plane P2 that extends through a bottom portion of the filter 11. The plane P1 and the plane P2 are parallel to each other. In addition, the average particle size of the biological product BP is, for example, 10 μm.

In addition, the support structures 3 preferably hold the frame 12 such that the capacity of a curved part of the filter 11 defined by the surface of the filter 11 and the plane P1 is equal to or greater than the total volume of the filtration target. With this configuration as well, the filtration treatment amount can be further increased by suppressing clogging of the filtration filter 1 to an even greater degree.

It is sufficient that the support structures 3 hold the frame 12 such that the filter 11 is in a bent state when the liquid containing the biological product BP is supplied to the filter 11. For example, the support structures 3 may hold the frame 12 in a fixed manner such that the filter 11 is always maintained in a bent state. Alternatively, the support structures 3 may be configured so as to have a mechanism that allows an inclination angle of the frame 12 with respect to a horizontal plane to be changed (for example, from 0° to 30°). With this configuration, for example, it is possible to bend the filter 11 when filtering is going to be performed, and not bend the filter 11 when filtering is not going to be performed. In this case, a load acting on the filter 11 as a result of the filter 11 being bent can be reduced. Furthermore, with this configuration, once the fluid has been supplied, the bending amount L1 of the filter 11 can be reduced. In this case, when the biological product BP is to be recovered, analyzed and so forth after the filtration has finished, the recovery, analysis and so forth can be performed in a state where the bending amount L1 of the filter 11 has been reduced.

Figure 5:
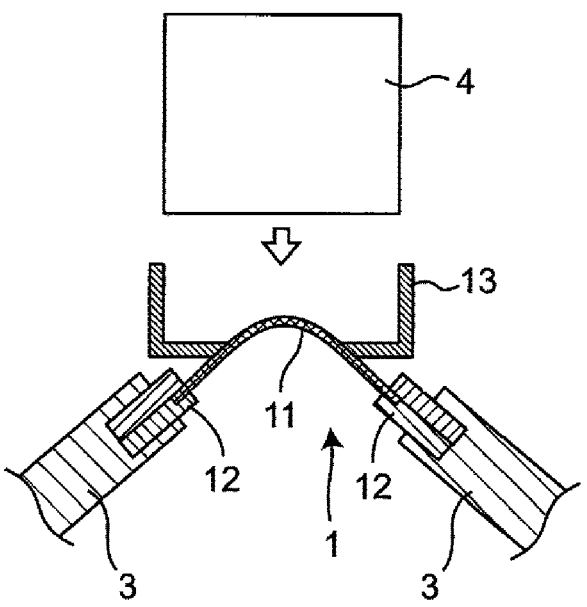
FIG. 5 is a sectional view illustrating a state in which support structures hold a frame in the filtration device illustrated in FIG. 3 such that a filter is bent toward a side that receives the pressure of a liquid.

Although the support structures 3 are configured to hold the frame 12 such that the filter 11 is bent toward the side that does not receive the pressure of the liquid in embodiment 1, the present invention is not limited to this configuration. For example, as illustrated in FIG. 5, the support structures 3 may be configured so as to hold the frame 12 such that the filter 11 is bent toward the side that receives the pressure of the liquid. With this configuration as well, blocking of the through holes 11a in a central portion of the filter 11 by the biological product BP is suppressed, and the filtration treatment amount can be increased by suppressing clogging of the filtration filter 1. In this case, a container 13, in which a through hole is provided to allow the filter 11 to protrude through a bottom surface of the container 13, may be arranged in order that the liquid supplied by the fluid supplying unit 4 does not flow into an area outside the filter 11.

Furthermore, it has been assumed in embodiment 1 that the filtration target is the biological product BP contained in a liquid, but the present invention is not so limited. For example, the filtration target may be a large-sized foreign body contained in a liquid. In addition, the filtration target may be a substance contained in a gas. In other words, it is sufficient that the filtration target be a substance contained in a fluid, and for example, the filtration target may be PM2.5 contained in air.

Furthermore, although it has been assumed that the filtration filter 1 and the filtration device 2 are used to filter the biological product BP from a liquid in embodiment 1, the present invention is not so limited. For example, the filtration filter 1 and the filtration device 2 may be used to concentrate a component contained in a liquid.

Figure 6:
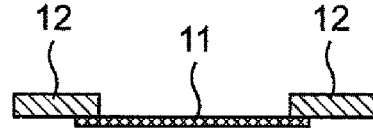
FIG. 6 is a sectional view illustrating an example in which a frame is connected to only one main surface of a filter.

In addition, although the frame 12 is configured so as to be connected to both main surfaces of the filter 11 in embodiment 1, the present invention is not limited to this configuration. As illustrated in FIG. 6, the frame 12 may be connected to only one main surface of the filter 11. In this case, since there is no need to provide the second layer member 22 on the other main surface of the filter 11, a reduction in cost can be achieved. Furthermore, since the flexibility of the frame 12 can be improved, it is possible to suppress the occurrence of damage to the frame 12 when the frame 12 is bent, for example.

Embodiment 2

Figure 7:
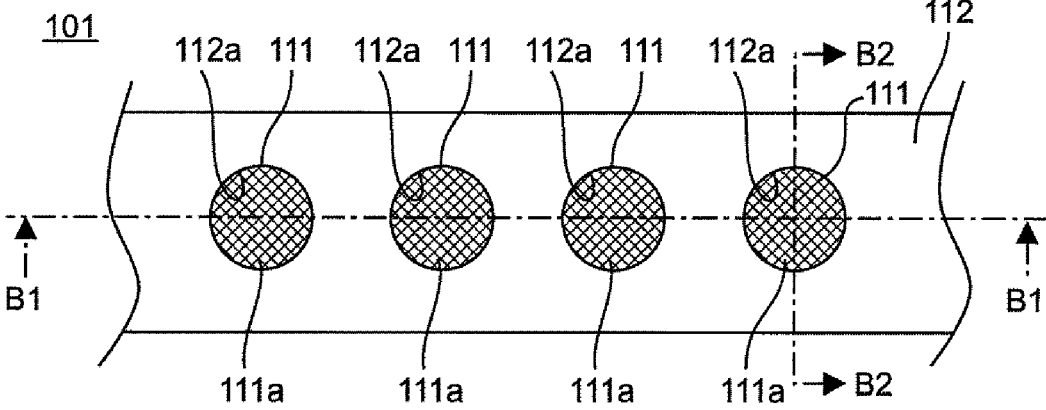
FIG. 7 is a schematic plan view of a filtration filter group used in a filtration device according to embodiment 2 of the present invention.
Figure 8:
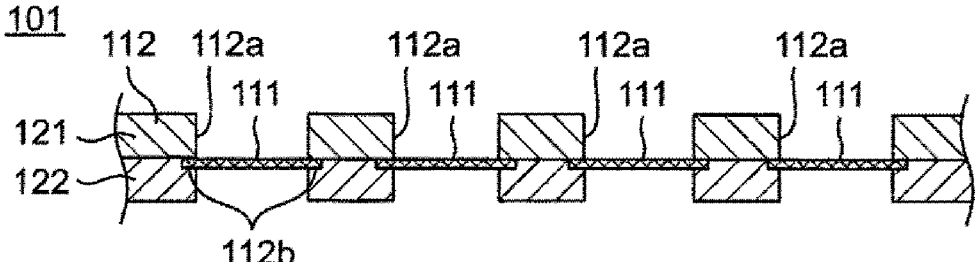
FIG. 8 is a sectional view taken along line B1-B1 in FIG. 7.
Figure 9:
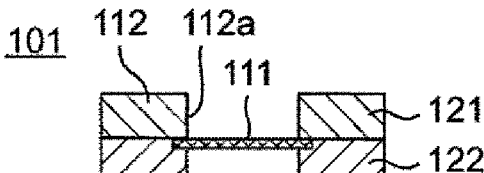
FIG. 9 is a sectional view taken along line B2-B2 in FIG. 7.

In embodiment 2, the filtration target is a biological product contained in a liquid, but the filtration target may instead be PM2.5 contained in a gas, for example, as described above. As illustrated in FIGS. 7 to 9, a filtration filter group 101 according to embodiment 2 includes a plurality of filters 111 and a frame 112 that holds the plurality of filters 111. In embodiment 2, each filter 111 is the same as the filter 11 described above, and therefore, detailed description thereof is omitted.

In embodiment 2, the frame 112 is a flexible tape-shaped member. A plurality of through holes 112a are provided in the frame 112. The plurality of through holes 112a are provided at regular intervals, for example, in a longitudinal direction of the frame 112. The shape and dimensions of the through holes 112a are appropriately set in accordance with a desired filtration treatment amount, filtration treatment time, and so forth. The through holes 112a have a circular shape when viewed from a main surface side of the frame 112, for example. The through holes 112a have a diameter of 6 mm, for example. The interval between the through holes 112a is 12 mm, for example.

The frame 112 is formed of an elastic member. Examples of the material of the frame 112 include polypropylene, polyester, polyurethane, rayon, polyvinyl chloride, hydrogel, nylon, polyolefin and paper. It is preferable that the material of the frame 112 be a material that can be sterilized in a variety of ways such as through gamma ray irradiation, an autoclave and ethylene gas. Examples of such a material include polyester, polyurethane and polyvinyl chloride. The width of the frame 112 is 12 mm, for example. The thickness of the frame 112 is 500 μm, for example.

In embodiment 2, the frame 112 has a two-layer structure and is formed of a first layer member 121 and a second layer member 122. The first layer member 121 is connected to one main surfaces of the filters 111 with, for example, an adhesive. The second layer member 122 is connected to the other main surfaces of the filters 111 with, for example, an adhesive. In other words, the frame 112 is connected to both opposed main surfaces of the filters 111. Thus, the filters 111 can be prevented from peeling off the frame 112 when the filtration filter group 101 is bent. The first layer member 121 and the second layer member 122 are connected to each other with, for example, an adhesive. The adhesive is preferably a non-water-soluble adhesive. Examples of such an adhesive include an epoxy based adhesive and a silylated-urethane-resin-based adhesive.

Recesses 112b are provided in the wall surfaces of the frame 112 that form the through holes 112a. The recess 112b are each formed, for example, in an annular shape. Outer peripheral portions of the filters 111 are fitted into the respective recesses 112b, and the filters 111 are thus held by the frame 112. Thus, the filters 111 are exposed to the outside from the through holes 112a of the frame 112. By providing the recesses 112b, shifting of the positions of the filters 111 can be suppressed, for example. It is sufficient for the recesses 112b to be provided in at least either of the first layer member 121 and the second layer member 122.

Next, description will be given of a filtration device 102 that filters a biological product by using the filtration filter group 101 according to embodiment 2.

Figure 10:
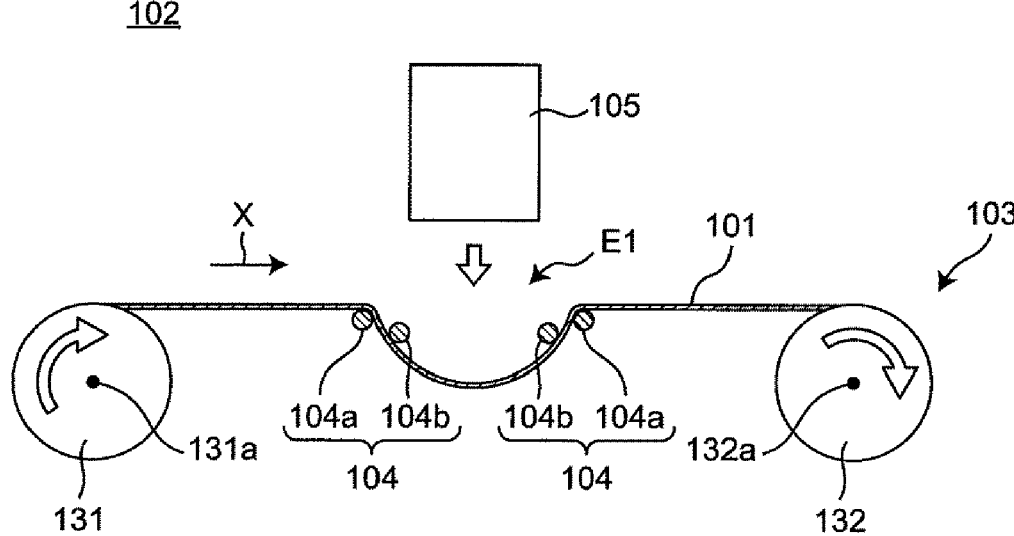
FIG. 10 is a schematic side view of the filtration device according to embodiment 2 of the present invention.

As illustrated in FIG. 10, the filtration device 102 includes a conveyer 103, two support structures 104 and a fluid supplying unit 105. The conveyer 103 conveys the filtration filter group 101 so that a filter 111 that is exposed from a specific through hole 112a is positioned in a fluid supply region E1 located between the two support structures 104. In addition, the conveyer 103 conveys the filtration filter group 101 such that the filter 111 that is positioned in the fluid supply region E1 successively changes. In embodiment 2, the conveyer 103 includes a supply reel 131 and a winding reel 132.

The filtration filter group 101 is wound around the supply reel 131. In addition, the supply reel 131 is provided with a feeding motor 131a. The filtration filter group 101 is fed from the supply reel 131 by driving the feeding motor 131a. The filtration filter group 101 fed from the supply reel 131 is wound up by the winding reel 132.

The winding reel 132 is provided with a winding motor 132a. For example, the winding motor 132a is driven, and as a result, a constant tension acts on the winding reel 132. Thus, the filtration filter group 101 fed from the supply reel 131 is wound around the winding reel 132 at the same time as the feeding operation.

The two support structures 104 are arranged between the supply reel 131 and the winding reel 132. More specifically, one support structure 104 is arranged upstream of the fluid supply region E1 relative to the direction in which the filtration filter group 101 is conveyed. The other support structure 104 is arranged downstream of the fluid supply region E1 relative to the direction in which the filtration filter group 101 is conveyed. Each support structure 104 is formed of a pair of guide rollers 104a and 104b. The filtration filter group 101 is conveyed by being sandwiched between the guide rollers 104a and the guide rollers 104b so as to be bent in the fluid supply region E1.

In addition, each support structure 104 is configured to have a mechanism that allows an inclination angle of the frame 112 with respect to a horizontal plane to be changed (for example, from 0° to 30°). In embodiment 2, each support structure 104 is configured so as to bend the filter 111 when filtering is going to be performed and so as to not bend the filter 111 when filtering is not going to be performed.

The fluid supplying unit 105 is provided so as to supply a liquid containing a biological product to the filter 111 that is exposed through a specific through hole 112a of the filtration filter group 101 that is bent by the support structures 104 in the fluid supply region E1.

Next, an example of operation of the filtration device 102 will be described. Operation of the filtration device 102 is controlled by a control unit (not illustrated) provided in the filtration device 102 on the basis of a program that is stored in advance.

First, the feeding motor 131a and/or the winding motor 132a are driven, and thereby the filter 111 that is exposed from a specific through hole 112a is conveyed to the fluid supply region E1.

Next, the support structures 104 hold the frame 112 such that the filter 111 is bent with respect to a plane that intersects (for example, is perpendicular to) the direction in which the fluid is going to be supplied.

After that, the fluid supplying unit 105 supplies the liquid containing the biological product to the filter 111 that is bent by the support structures 104. Supply of the liquid containing the biological product continues for a fixed period of time, for example, for a period of time that it is estimated to take for the filter 111 to become clogged.

Next, the support structures 104 hold the frame 112 so as to bend the filter 111. After that, the feeding motor 131a and/or the winding motor 132a are driven, and thereby, the filter 111 that is to perform filtering next (for example, the filter exposed from the through hole adjacent to the specific through hole) is conveyed to the fluid supply region E1. Thus, the filter 111 positioned in the fluid supply region E1 is replaced.

Hereafter, similarly, the filter 111 conveyed to the fluid supply region E1 is bent by the support structures 104 and the fluid is supplied to the bent filter 111 by the fluid supplying unit 105. In addition, the filter 111 positioned in the fluid supply region E1 is replaced by the conveyer 103.

According to embodiment 2, the fluid supplying unit 105 supplies the liquid containing the biological product in a state where the support structures 104 bend the filter 111. As a result, the amount of biological product that would be required to block all the through holes 111a of the filter 111 can be increased. Thus, blocking of the through holes 111a in a peripheral portion of the filter 111 by the biological product is suppressed, and consequently, clogging of the filtration filter can be suppressed. As a result, the filtration treatment amount of the filtration filter can be increased compared with the related art. Here, as described above, "bending" does not only refer to bending in an arc-like shape. For example, the meaning of "bending" also includes bending (curving) at an acute angle, a right angle and an obtuse angle.

In addition, according to embodiment 2, the conveyer 103 conveys the filtration filter group 101 such that the filter 111 that is positioned in the fluid supply region E1 is successively changed, and therefore, the filter 111 can be easily replaced.

Furthermore, according to embodiment 2, since a plurality of filters 111 are held by one frame 112, when a specific filter 111 becomes clogged, the specific filter 111 can be replaced with another filter 111 by simply moving the frame 112. Therefore, a filtration filter can be easily replaced. In addition, entry of foreign matter (contamination) can be reduced by replacing a filtration filter.

Furthermore, according to embodiment 2, the support structures 104 are configured to have a mechanism that allows the inclination angle of the frame 112 with respect to a horizontal plane to be changed. With this configuration, for example, it is possible to bend the filter 111 when filtering is going to be performed, and not bend the filter 111 when filtering is not going to be performed. In this case, a load acting on a filter 111 as a result of the filter 111 being bent can be reduced. Furthermore, with this configuration, once the fluid has been supplied, the bending amount of the filter 111 can be reduced. In this case, when the biological product is to be recovered, analyzed and so forth after the filtration has finished, the recovery, analysis and so forth can be performed in a state where the bending amount of the filter 111 has been reduced.

In addition, according to embodiment 2, since the frame 112 is a flexible tape-shaped member, the filtration filter group 101 can be stored in a compact form by being wound up and can be deformed into an arbitrary shape, and therefore convenience is improved.

Furthermore, according to embodiment 2, a plurality of filters 111 are provided so as to respectively correspond to the plurality of through holes 112a. In other words, a configuration is adopted in which one filter 111 is provided for one through hole 112a. Thus, compared with providing a filter 111 in a similar-sized area to the frame 112, the area in which the filter 111 is provided can be reduced and a reduction in cost can be achieved.

It is preferable that the bending amount of the filter 111, which is caused by the frame 112 being held by the support structures 104, be larger than the bending amount of the filter 111 caused by the pressure of the liquid during a filtering operation. For example, the support structures 104 preferably hold the frame 112 such that the bending amount of an exposed portion of the filter 111 that is not held by the frame 112 is at least two times the average particle diameter of the biological product. With this configuration, the filtration treatment amount can be further increased by suppressing clogging of the filtration filter to an even greater degree. Since the description of the bending amount of an exposed portion of the filter 111 is the similar to that for the bending amount of an exposed portion of the filter 11 given above using FIG. 4, detailed description of the bending amount is omitted here.

In addition, it is preferable that the support structures 104 hold the frame 112 such that the capacity of a curved part of the filter 111 defined by the surface of the filter 111 and a plane that extends through outer peripheral end portions of the exposed portion of the filter 111 be equal to or greater than the total volume of the filtration target. With this configuration as well, the filtration treatment amount can be further increased by suppressing clogging of the filtration filter even more.

Figure 11:
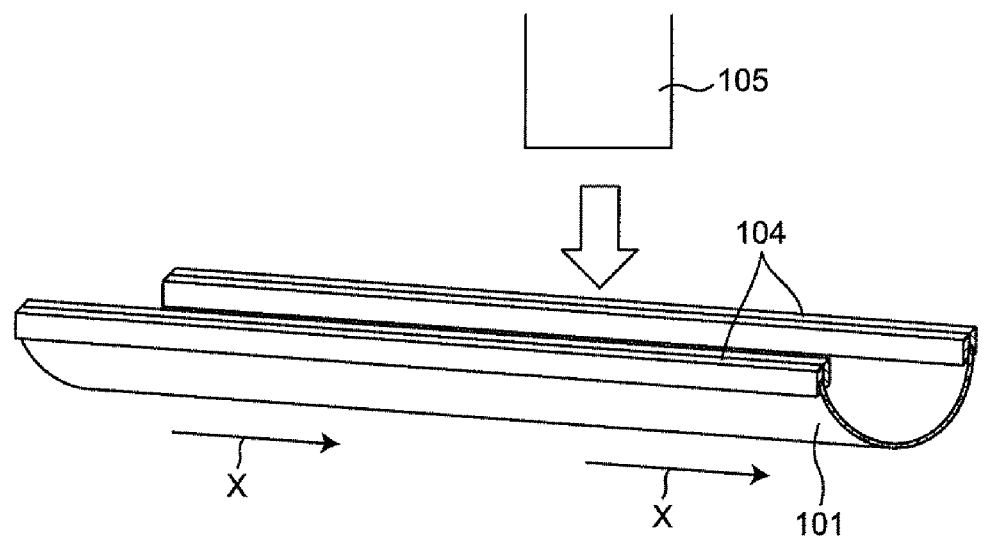
FIG. 11 is a perspective view illustrating a state in which the filtration filter group of FIG. 7 is bent in a lateral direction.
Figure 12:
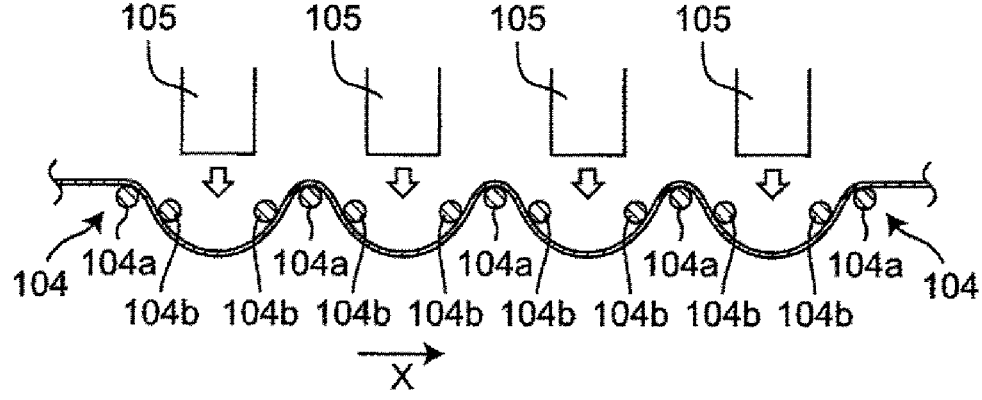
FIG. 12 is a side view illustrating a state in which the filtration filter group of FIG. 7 is made to deform in a wave-like manner in a direction of conveying performed by a conveyer.

In addition, in embodiment 2, as illustrated in FIG. 10, the support structures 104 are configured such that the filtration filter group 101 is bent in an area along part of the longitudinal direction thereof (conveying direction X of conveying performed by the conveyer 103), but the present invention is not so limited. For example, as illustrated in FIG. 11, two support structures 104 may be configured such that the filtration filter group 101 is bent in a lateral direction. Furthermore, as illustrated in FIG. 12, support structures 104 may be configured such that the filtration filter group 101 (frame 112) is deformed in a wave-like manner along the conveying direction of conveying performed by the conveyer 103. In addition, in this case, as illustrated in FIG. 12, adjacent support structures 104 may be configured so as to share one guide roller 104a. With this configuration, each filter 111 held by the frame 112 can be easily bent. In addition, since a plurality of filters 111 can be simultaneously bent, the filtration treatment amount can be increased and the filtration time can be shortened by simultaneously supplying a liquid containing a biological product to the plurality of filters 111 from a plurality of fluid supplying units 105.

Figure 13:
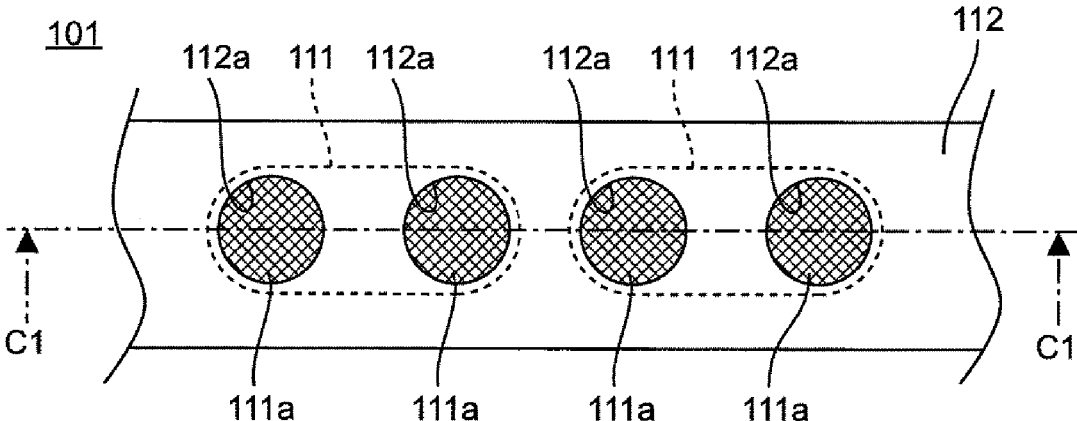
FIG. 13 is a plan view illustrating a schematic configuration representing a modification of the filtration filter group of FIG. 7.
Figure 14:
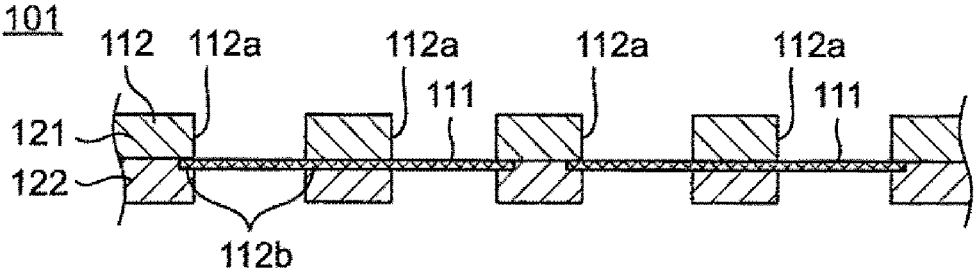
FIG. 14 is a sectional view taken along line C1-C1 in FIG. 13.

Furthermore, in embodiment 2, a configuration is adopted in which one filter 111 is provided for one through hole 112a, but the present invention is not limited to this configuration. For example, a filter 111 may be formed to have a size that encompasses two or more through holes 112a when viewed from a thickness direction of the filtration filter group 101, as illustrated in FIGS. 13 and 14. In other words, one filter 111 may be formed so as to be exposed from two or more through holes 112a.

Figure 15:
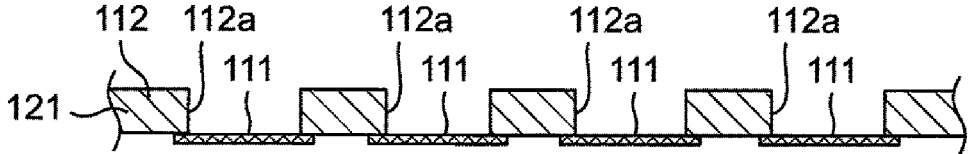
FIG. 15 is a sectional view illustrating an example in which a frame is connected to only one main surface of a filter.

In addition, although the frame 112 is configured so as to be connected to both main surfaces of the filters 111 in embodiment 2, the present invention is not so limited. As illustrated in FIG. 15, the frame 112 may be connected to only one main surfaces of the filters 111. In this case, since there is no need to provide the second layer member 122 on the other main surfaces of the filters 111, a reduction in cost can be achieved. In addition, since the flexibility of the frame 112 can be improved, it is possible to suppress the occurrence of damage to the frame 112 when the frame 112 is bent, for example.

Furthermore, although a configuration is adopted in which the filters 111 are conveyed to the fluid supply region E1 by conveying the filtration filter group 101 using the conveyer 103 in embodiment 2, the present invention is not so limited. It is sufficient for the conveyer 103 to be configured to convey the filters 111 to the fluid supply region E1 by conveying at least one of the filtration filter group 101 and the fluid supplying unit 105 as long as there is relative movement between the filters and the fluid supply region. In addition, a sterilization step may be provided before conveying a filter 111 to the fluid supply region E1. By providing a sterilization step, the entry of foreign matter (contamination) can be reduced.

Figure 16:
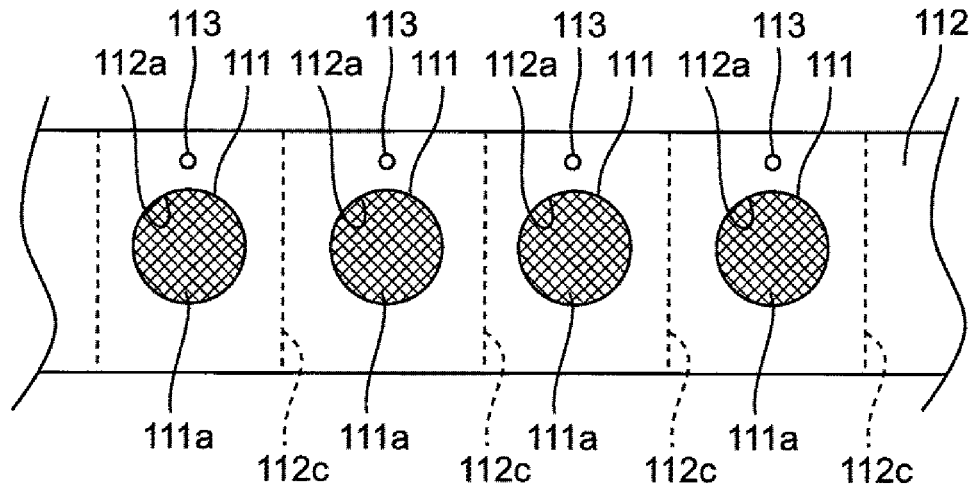
FIG. 16 is a plan view illustrating an example in which cutting lines and feeding holes are formed in a frame.

In addition, as illustrated in FIG. 16, cutting lines 112c may be provided between adjacent through holes 112a in the frame 112. With this configuration, a filtration filter group 101 of a desired length can be obtained by cutting along the cutting lines 112c, and the ease of handling the filtration filter group 101 can be further improved. For example, by cutting a part of the frame 112 that includes a filter 111 that has filtered a biological product along the cutting lines 112c, the part of the frame 112 can be analyzed using a microscope or the like.

In addition, as illustrated in FIG. 16, a plurality of feeding holes 113 may be provided in the frame 112. It is sufficient for the plurality of feeding holes 113 to be provided at regular intervals in a longitudinal direction of the frame 112, for example. Furthermore, in this case, for example, it is sufficient for a configuration to be adopted in which the conveyer 103 includes wheels (not illustrated) that are each equipped with a plurality of pins that correspond to the plurality of feeding holes 113. Thus, the filtration filter group 101 can be more accurately conveyed a desired distance, and the precision with which the filter 111 is positioned in the fluid supply region E1 can be improved.

Figure 17:
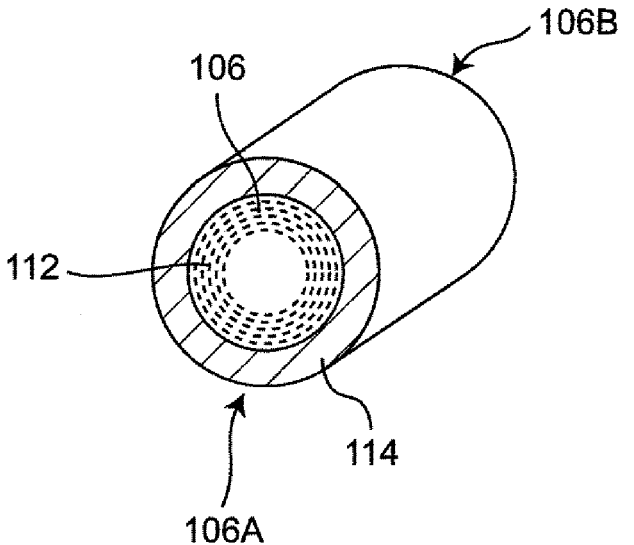
FIG. 17 is a perspective view illustrating an example in which a protective sheet is provided on an outermost peripheral surface of a roll body obtained by winding the filtration filter group of FIG. 7 into a roll.

Furthermore, as illustrated in FIG. 17, a protective sheet 114 may be provided on an outermost peripheral surface of a roll body 106 obtained by winding the frame 112 (filtration filter group 101) into a roll. In addition, a protective sheet (not illustrated) may be provided on at least one of a pair of opposing base surfaces 106A and 106B of the roll body 106. With this configuration, the filtration filter group can be prevented from becoming dirty, damaged and so forth, and ease of handling the filtration filter group can be further improved.

Figure 18:
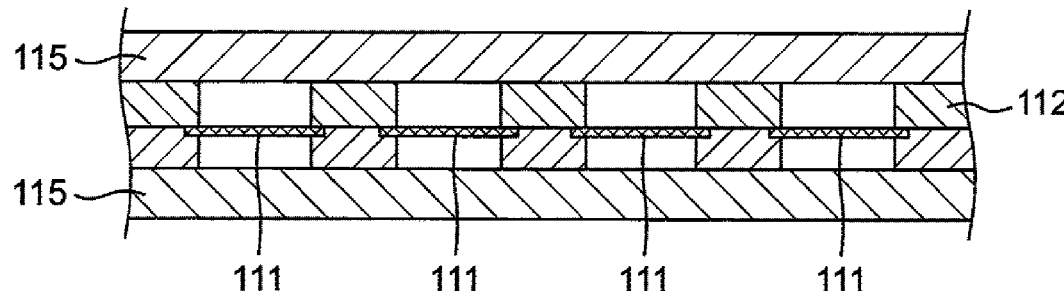
FIG. 18 is a sectional view illustrating an example in which protective sheets are provided on both main surfaces of the filtration filter group of FIG. 7.

In addition, as illustrated in FIG. 18, protective sheets 115 that cover the filters 111 that are exposed in a plurality of places may be provided on both main surfaces of the frame 112. With this configuration, the filtration filter group 101 can be prevented from becoming dirty, damaged and so forth, and the ease of handling the filtration filter group 101 can be further improved. A protective sheet 115 may be provided on only one main surface of the frame 112 in the case where the frame 112 is wound into a roll, for example. With this configuration, the flexibility of the frame 112 can be improved.

It is sufficient for the protective sheets to be formed a material having flexibility such as polystyrene, polyethylene, polyester, polyurethane, rayon, PVC, hydrogel, nylon, polyolefin and cellulose, for example. The material of the protective sheets is preferably a material that can be sterilized in a variety of ways such as through gamma ray irradiation, an autoclave and ethylene gas. Examples of such a material include polyester, polyurethane and polyvinyl chloride.

Embodiment 3

A filtration filter 1A according to embodiment 3 differs from the filtration filter 1 according to embodiment 1 in that the filter 11 is held by the frame 12 so as to be maintained in a bent state. In other words, in embodiment 3, the filter 11 is held by the frame 12 in a pre-bent state, rather than being forcibly bent by the support structures 3.

According to embodiment 3, since the filter 11 is held by the frame 12 so as to be maintained in a bent state, the amount of biological product BP that would be required to block all the through holes 11a of the filter 11 can be increased. Thus, the filtration treatment amount can be increased by suppressing clogging of the filtration filter 1A even more. Furthermore, according to embodiment 3, the necessity of equipping the filtration device with the support structures 3, which were described above using FIGS. 3 to 5, can be eliminated.

13

Figure 19:
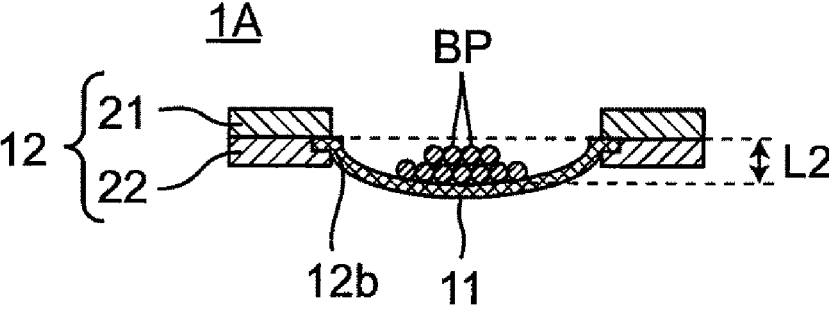
FIG. 19 is a schematic sectional view of a filtration filter used in a filtration device according to embodiment 3 of the present invention.
Figure 20:
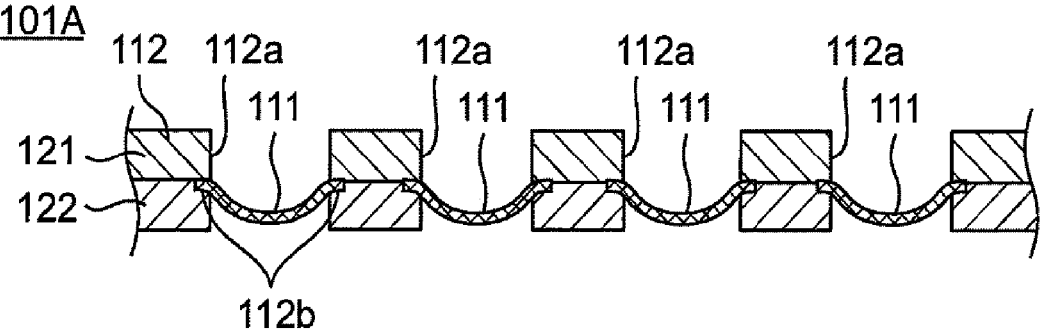
FIG. 20 is a schematic sectional view of a filtration filter group used in a filtration device according to embodiment 4 of the present invention.

It is preferable that the bending amount of the filter 11 be larger than the bending amount of the filter 11 caused by pressure of the fluid during filtering. For example, as illustrated in FIG. 19, a bending amount L2 of an exposed portion of the filter 11 that is not held by the frame 12 is preferably at least two times the average particle diameter of the filtration target. Alternatively, it is preferable that the filter 11 be held by the frame 12 such that the capacity of a curved part of the filter 11 defined by the surface of the filter 11 and a plane that extends through outer peripheral end portions of the exposed portion of the filter 11 is equal to or greater than the total volume of the filtration target. With this configuration as well, the filtration treatment amount can be further increased by suppressing clogging of the filtration filter even more.

Embodiment 4

A filtration filter group 101A according to embodiment 4 differs from the filtration filter group 101 according to embodiment 2 in that the filters 111 are held by the frame 112 so as to be maintained in a bent state. In other words, in embodiment 4, the filters 111 are held by the frame 112 in a pre-bent state, rather than being forcibly bent by the support structures 104.

According to embodiment 4, since the filters 111 are held by the frame 112 so as to be maintained in a bent state, the amount of biological product BP that would be required to block all the through holes 111a of the filters 111 can be increased. Thus, the filtration treatment amount can be increased by suppressing clogging of the filtration filter group 101A. Furthermore, according to embodiment 4, the necessity of equipping the filtration device with the support structures 104, which were described above using FIGS. 10 to 12, can be eliminated.

It is preferable that the bending amount of the filters 111 be larger than the bending amount of the filters 111 caused by the pressure of the fluid during filtering. For example, a bending amount of an exposed portion of a filter 111 that is not held by the frame 112 is preferably at least two times the average particle diameter of the filtration target. Alternatively, it is preferable that the filters 111 be held by the frame 112 such that the capacity of a curved part of each filter 111 defined by the surface of the filter 111 and a plane that extends through outer peripheral end portions of the exposed portion of the filter 111 is equal to or greater than the total volume of the filtration target. With this configuration as well, the filtration treatment amount can be further increased by suppressing clogging of the filtration filter even more.

In addition, the various respective effects of the embodiments can be achieved by appropriately combining any of the various embodiments described above.

Although the present invention has been sufficiently described in the form of preferred embodiments while referring the accompanying drawings, various modifications and amendments would be clear to a person skilled in the art. Such modifications and amendments are to be understood as being included in the scope of the present invention so long as the modifications and amendments do not deviate from the scope of the present invention defined by the appended claims.

The present invention can increase a filtration treatment amount by suppressing clogging of a filtration filter, and therefore, the present invention is of use in filtration devices and filtration methods that filter a filtration target contained in a fluid such as a biological product or PM2.5.

REFERENCE SIGNS LIST 1, 1A filtration filter
2 filtration device
3 support structure
4 fluid supplying unit
11 filter
11a through hole
12 frame
12b recess
13 container
21 first layer member
22 second layer member
101, 101A filtration filter group
102 filtration device
103 conveyer
104 support structure
104a, 104b guide roller
105 fluid supplying unit
106 roll body
111 filter
111a through hole
112 frame
112a through hole
112b recess
112c cutting line
113 feeding hole
114, 115 protective sheet
121 first layer member
122 second layer member
131 supply reel
132 winding reel
201 filtration filter
201a through hole
202 biological product

The invention claimed is:
1. A filtration device comprising:
a filter assembly including a frame and a filter, the frame holding an outer peripheral portion of the filter to form an exposed contiguous inner section of the filter having a single contiguous outer periphery, the exposed inner section of the filter having openings through which a fluid can pass but a filtration target contained in the fluid cannot pass, the filter assembly being bendable between a flat position wherein the filter lies in a plane and various bent positions wherein the filter is bent, the frame fully surrounding and enclosing the exposed contiguous inner section of the filter when the filter assembly is in the flat position;
an inanimate support structure that holds the frame in such a manner that that the frame, and with it the exposed contiguous inner section of the filter, is bent into a first bent position, which extends outside of the plane, by the inanimate support structure itself, the inanimate support structure holding the frame in such a manner that the fluid is free to pass through the entire exposed contiguous inner section of the filter but is not free to pass through the outer peripheral portion of the filter; and
a fluid supply that supplies the fluid containing the filtration target to the exposed contiguous inner section of the filter while the frame is held in the first bent position by the inanimate support structure, the exposed contiguous inner section of the filter not being supported so that it is free to bend beyond the first bent position in a flow direction of the fluid as the fluid passes through the exposed contiguous inner section of the filter.

2. The filtration device according to claim 1, wherein the inanimate support structure holds the frame in such a manner that the filter is bent in the flow direction of the fluid.

3. The filtration device according to claim 1, wherein the filtration target is a biological product and the filter is a metal film having a plurality of through holes, the metal film being adapted to separate the biological product from the fluid.

4. The filtration device of claim 1, wherein the exposed contiguous inner section of the filter has first and second opposed major unsupported surfaces.

5. The filtration device according to claim 1, wherein the exposed contiguous inner section of the filter has a curved portion when the frame is in the first bent position.

6. The filtration device according to claim 1, wherein the exposed contiguous inner section of the filter is round when the filter assembly is in the flat position.

7. The filtration device according to claim 1, wherein the amount that the filter is bent when it is in the first bent position is at least two times an average particle diameter of the filtration target.

8. The filtration device according to claim 1, wherein the amount of the filtration target that can be captured on the exposed contiguous inner section of the filter is greater than or equal to the total volume of the filtration target.

9. The filtration device according to claim 1, wherein the inanimate support structure bends the filter assembly at an angle and the inanimate support structure is adjustable so as to allow the angle that the filter assembly is bent to be adjusted.

10. The filtration device according to claim 1, wherein the fluid is a liquid.

11. The filtration device according to claim 1, wherein the exposed, contiguous outer periphery of the filter is circular in shape.

12. The filtration device according to claim 1, wherein the fluid supply supplies the fluid to the entire exposed contiguous inner section of the filter.

13. The filtration device according to claim 1, wherein the exposed contiguous inner section of the filter is ovoid in shape when the filter assembly lies in the flat position.

14. The filtration device according to claim 1, wherein the exposed contiguous inner section of the filter is circular in shape when the filter assembly lies in the flat position.

15. The filtration device according to claim 1, wherein the filter assembly includes a single filter.

16. The filtration device according to claim 1, wherein the amount that the exposed contiguous inner section of the filter is bent by the fluid passing there through is smaller than the amount that the exposed contiguous inner section of the filter is bent by the inanimate support structure.

17. The filtration device according to claim 16, wherein the inanimate support structure is a mechanical, non-human, structure.

18. The filtration device according to claim 16, wherein the inanimate support structure holds the frame in such a manner that the filter is bent against the flow direction of the fluid.

19. The filtration device according to claim 1, wherein the inanimate support structure does not contact the exposed contiguous inner section of the filter.

20. The filtration device according to claim 1, wherein the contiguous inner section of the filter has a rounded portion surrounded by a pair of planar portions when the filter is bent into the first bent position.

21. The filtration device according to claim 1, wherein an inner peripheral portion of the frame defines the single contiguous outer periphery of the exposed contiguous inner section of the filter.

22. The filtration device according to claim 1, wherein the frame is not integral with the filter.

23. The filtration device according to claim 22, wherein the frame overlaps an outermost section of the filter.

24. The filtration device according to claim 22, wherein the frame and the filter are made of different materials.

25. The filtration device according to claim 1, wherein the frame holds the filter in the flat position before the frame is held by the inanimate support structure.

* * * * *